(12) United States Patent
Matsui et al.

(10) Patent No.: US 8,714,015 B2
(45) Date of Patent: May 6, 2014

(54) JOINT QUALITY INSPECTION AND JOINT QUALITY INSPECTION METHOD

(75) Inventors: Nami Matsui, Komaki (JP); Youichirou Baba, Miyoshi (JP); Hironari Matsubara, Nagoya (JP); Yoshinobu Tamura, Toyota (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 290 days.

(21) Appl. No.: 13/259,010

(22) PCT Filed: Mar. 31, 2009

(86) PCT No.: PCT/JP2009/056644
§ 371 (c)(1),
(2), (4) Date: Sep. 22, 2011

(87) PCT Pub. No.: WO2010/113250
PCT Pub. Date: Oct. 7, 2010

(65) Prior Publication Data
US 2012/0011934 A1   Jan. 19, 2012

(51) Int. Cl.
*G01N 29/04* (2006.01)
(52) U.S. Cl.
USPC ............................................. 73/582; 73/588
(58) Field of Classification Search
USPC ........... 73/588, 627, 628, 653, 654, 655, 657, 73/661, 582; 702/35, 40
See application file for complete search history.

(56) References Cited

U.S. PATENT DOCUMENTS

| | | | | |
|---|---|---|---|---|
| 4,246,793 A | * | 1/1981 | Fairand et al. | 73/628 |
| 4,554,836 A | * | 11/1985 | Rudd | 73/657 |
| 4,641,527 A | * | 2/1987 | Hiroi et al. | 73/582 |
| 5,099,693 A | * | 3/1992 | Payne et al. | 73/632 |
| 5,457,997 A | * | 10/1995 | Naruo et al. | 73/643 |
| 5,505,090 A | * | 4/1996 | Webster | 73/657 |
| 5,719,952 A | * | 2/1998 | Rooks | 382/150 |
| 6,182,512 B1 | * | 2/2001 | Lorraine | 73/655 |
| 6,525,811 B1 | * | 2/2003 | Paladino et al. | 356/237.1 |
| 6,747,268 B1 | * | 6/2004 | Ume | 250/227.11 |
| 7,492,449 B2 | * | 2/2009 | Ume et al. | 356/237.1 |

FOREIGN PATENT DOCUMENTS

| | | |
|---|---|---|
| JP | 62-076731 A | 4/1987 |
| JP | 05-082599 A | 4/1993 |
| JP | 11-345835 A | 12/1999 |
| JP | 2000-150563 A | 5/2000 |
| JP | 2004-047944 A | 2/2004 |
| JP | 2004-335941 A | 11/2004 |
| JP | 2008-108960 A | 5/2008 |

* cited by examiner

*Primary Examiner* — Helen Kwok
(74) *Attorney, Agent, or Firm* — Gifford, Krass, Sprinkle, Anderson & Citkowski, P.C.

(57) ABSTRACT

A joint quality examining device and method for accurately examining in real time the qualities of the joints of all the products where joining members are joined to members to be joined. A joining device includes an ampere meter, a frequency meter, an encoder, and a recording unit the four for detected the joining waveform produced in a joining process, a feature point extracting unit for extracting from the deleted joining waveform a feature point related to an after-endurance physical quantity usable for evaluation of the quality which the joint is required to have after an endurance test, a calculating formula setting unit storing the calculation formula for calculating the after-endurance physical quantity, a calculating unit for calculating the after-endurance physical quantity of the joint from the feature point extracted by using the calculation formula, and a judging unit for judging whether or not the joint quality of the joint is acceptable on the basis of the comparison of the calculated after-endurance physical quantity and a predetermined threshold.

8 Claims, 8 Drawing Sheets

A: Stationary state
B: Oxide film removing state
C: bonding area increasing state
D: Stabilizing state
U: Ultrasound

FIG. 6

|     | X1    | X2    | X3    | X4    | X5    | X6    | X7    | X8    | X9    | X10   | X11   | X12   | X13   | X14   | X15   | X16   | X17   | X18   | X19   |
|-----|-------|-------|-------|-------|-------|-------|-------|-------|-------|-------|-------|-------|-------|-------|-------|-------|-------|-------|-------|
| X1  | X1    |       |       |       |       |       |       |       |       |       |       |       |       |       |       |       |       |       |       |
| X2  | 0.22  | X2    |       |       |       |       |       |       |       |       |       |       |       |       |       |       |       |       |       |
| X3  | 0.27  | 0.03  | X3    |       |       |       |       |       |       |       |       |       |       |       |       |       |       |       |       |
| X4  | 0.76  | 0.24  | 0.67  | X4    |       |       |       |       |       |       |       |       |       |       |       |       |       |       |       |
| X5  | 0.64  | 0.19  | 0.40  | 0.72  | X5    |       |       |       |       |       |       |       |       |       |       |       |       |       |       |
| X6  | -0.71 | -0.18 | -0.38 | -0.70 | -0.59 | X6    |       |       |       |       |       |       |       |       |       |       |       |       |       |
| X7  | 0.74  | 0.21  | 0.43  | 0.79  | 0.94  | -0.83 | X7    |       |       |       |       |       |       |       |       |       |       |       |       |
| X8  | 0.26  | -0.03 | 0.25  | 0.29  | 0.28  | -0.76 | 0.51  | X8    |       |       |       |       |       |       |       |       |       |       |       |
| X9  | 0.87  | 0.20  | 0.27  | 0.79  | 0.72  | -0.76 | 0.82  | 0.34  | X9    |       |       |       |       |       |       |       |       |       |       |
| X10 | -0.80 | -0.31 | -0.29 | -0.74 | -0.59 | 0.64  | -0.67 | 0.01  | -0.76 | X10   |       |       |       |       |       |       |       |       |       |
| X11 | 0.13  | 0.09  | 0.42  | 0.29  | 0.19  | -0.11 | 0.17  | -0.13 | 0.05  | -0.32 | X11   |       |       |       |       |       |       |       |       |
| X12 | 0.70  | 0.12  | 0.31  | 0.70  | 0.64  | -0.63 | 0.70  | 0.39  | 0.89  | -0.51 | 0.09  | X12   |       |       |       |       |       |       |       |
| X13 | 0.85  | 0.21  | 0.42  | 0.88  | 0.79  | -0.79 | 0.88  | 0.42  | 0.97  | -0.73 | 0.11  | 0.90  | X13   |       |       |       |       |       |       |
| X14 | 0.16  | 0.00  | 0.07  | 0.20  | 0.13  | 0.10  | 0.10  | -0.15 | 0.20  | -0.22 | 0.17  | 0.22  | 0.19  | X14   |       |       |       |       |       |
| X15 | -0.01 | 0.00  | -0.14 | -0.15 | -0.27 | -0.24 | 0.03  | -0.19 | -0.09 | -0.02 | -0.03 | -0.15 | -0.16 | -0.29 | X15   |       |       |       |       |
| X16 | -0.14 | -0.05 | -0.12 | 0.06  | 0.02  | 0.03  | 0.13  | 0.11  | -0.09 | 0.16  | -0.08 | -0.08 | -0.07 | -0.48 | -0.26 | X16   |       |       |       |
| X17 | -0.14 | -0.03 | -0.15 | -0.11 | 0.02  | -0.08 | 0.02  | 0.17  | -0.18 | 0.24  | -0.24 | -0.20 | -0.16 | -0.86 | 0.12  | 0.38  | X17   |       |       |
| X18 | 0.10  | -0.02 | 0.09  | 0.13  | -0.03 | 0.10  | -0.08 | -0.04 | 0.14  | -0.09 | 0.07  | 0.20  | 0.17  | 0.85  | -0.48 | -0.43 | -0.52 | X18   |       |
| X19 | -0.09 | -0.03 | 0.12  | 0.02  | -0.10 | 0.09  | 0.09  | 0.26  | -0.08 | 0.16  | -0.06 | -0.03 | -0.01 | -0.50 | -0.23 | 0.31  | 0.59  | -0.18 | X19   |
| X20 | 0.06  | 0.02  | -0.10 | -0.05 | 0.09  | -0.20 | -0.10 | -0.02 | -0.02 | -0.10 | 0.02  | -0.08 | -0.09 | 0.02  | 0.88  | -0.70 | -0.10 | -0.14 | -0.32 |
|     | 0.85  | 0.21  | 0.42  | 0.87  | 0.79  | -0.80 | 0.88  | 0.43  | 0.97  | -0.73 | 0.10  | 0.89  | 0.99  | 0.10  | -0.11 | -0.02 | -0.10 | 0.06  | 0.01  |

0.9 OR MORE

JOINT QUALITY INSPECTION AND JOINT QUALITY INSPECTION METHOD

CROSS-REFERENCE TO RELATED APPLICATIONS

This is a 371 national phase application of PCT/JP2009/056644 filed on Mar. 31, 2009, the entire contents of which are incorporated herein by reference.

TECHNICAL FIELD

The present invention relates to a joint quality inspection apparatus and a joint quality inspection method for inspecting the quality of a joint of a bonding item (for example a wire (metal conductor), etc) bonded to a bonding target member (for example a wiring terminal of an electronic component such as a semiconductor device, etc).

BACKGROUND ART

Known conventional switching devices include power semiconductor devices for large current applications such as IGBTs (Insulated Gate Bipolar Transistor), power MOS-FETs, and power transistors, etc. Meanwhile, hybrid cars and electric cars have drawn attention in recent years from the viewpoint of environment preservation or the like. An inverter device mounted in such a hybrid vehicle or the like is configured, for example, primarily with IGBT devices soldered on an insulating substrate, this insulating substrate with IGBT devices joined thereon being soldered to a base member that forms a housing of the inverter device.

The IGBT devices joined to the base member via the insulating substrate are electrically connected to a circuit wiring or other electronic components, etc formed on the base member by metal conductors.

Aluminum wires, for example, are used as the metal conductors for connecting the IGBT devices with other circuit wirings. The aluminum wire is bonded by wire bonding to the IGBT devices and other circuit wirings, etc to connect them.

Because of the recent demand for IGBT devices with higher current density, a sufficient area needs to be secured for the metal conductors and their joints since a large current will flow through the metal conductors connecting the IGBT devices with other circuit wirings, etc. To secure the area, typically, the number of wires, or the bonding area per one wire will have to be increased. Since an increase in the number of wires leads to an increase in the processing cost, metal conductors formed in a tape-like shape (wide, thin plate-like shape) to have a larger cross-sectional area (tape material) are increasingly used instead of wires having larger electrical resistance.

When connecting an IGBT device with another circuit wiring, etc with a wire or tape material, the wire or tape material is brought into contact with a wiring terminal of the IGBT device or another circuit wiring, and in this state, using a bonding tool of a bonding apparatus, for example, it is subjected to pressing load and ultrasonic vibration, whereby the wire or tape material is ultrasonically joined to the wiring terminal of the IGBT device or another circuit wiring.

The joint between the wire or tape material and the wiring terminal of the IGBT device is evaluated by, for example, detecting ultrasound applied to the bonding tool, and by comparing a detected ultrasound waveform with a predetermined reference ultrasound waveform (see Patent Document 1). The joint may also be evaluated by detecting the height of a lead wire (metal conductor) from the bonding surface and by determining whether or not the height is within a predetermined range (see Patent Document 2).

RELATED ART DOCUMENTS

Patent Documents

Patent Document 1: JP62 (1987)-076731A
Patent Document 2: JP05 (1993)-082599A

DISCLOSURE OF THE INVENTION

Problems to be Solved by the Invention

However, the conventional techniques described above have problems that, while it could be determined whether or not the wire or tape material and the wiring terminal were joined (connected) to each other, the quality of the joint including its reliability could not be evaluated. This is because, in order to evaluate the quality of the joint including its reliability, it is necessary to determine, for example, whether or not a certain current flow area will be secured, i.e., whether or not the bonding area can be maintained at a certain level or above throughout the life of the product, but no such determination is done in the conventional techniques described above.

To evaluate the joint quality, it is necessary to carry out a durability test such as a thermal shock test and to measure the physical quantities of the joint such as the bonding area after the test. However, it is practically impossible to carry out a durability test to each one of the products, and therefore in actuality, accurate evaluation of the joint quality including its reliability of all the products in real time is not available.

Accordingly, the present invention is devised to solve the problem described above, and its object is to provide a joint quality inspection apparatus and a joint quality inspection method, with which accurate real-time inspection of the joint quality including its reliability can be achieved for all the products in which a bonding item is joined to a bonding target member.

Means of Solving the Problems

One aspect of the present invention made to solve the above problem provides a joint quality inspection apparatus for inspecting a quality of a joint formed through ultrasonic joining of a bonding item to a bonding target member by applying ultrasound to a tool while pressing the bonding item with the tool, the apparatus comprising: a joining waveform detecting means for detecting at least one of joining waveforms generated during a bonding process; a characteristic feature extracting means for extracting, from the joining waveform detected by the joining waveform detecting means, a characteristic feature having a correlation with a post-durability-test physical quantity based on which a quality required for the joint after a durability test can be evaluated; and a quality evaluation means for evaluating the joint quality of the joint based on evaluation of replication probability of a bonding process in which good joint quality is ensured by comparing the characteristic feature extracted by the characteristic feature extracting means with a characteristic feature of that bonding process.

In this joint quality inspection apparatus, at least one of the joining waveforms generated during the bonding process is detected by the joining waveform detecting means. Here, it is preferable to detect joining waveforms associated with a deformation amount of the bonding item and an amplitude of the tool with the joining waveform detecting means, and it is even more preferable to also detect a joining waveform associated with a vibration frequency of the tool. This is because, by thus detecting a plurality of joining waveforms, the replication probability of the bonding process can be evaluated with improved accuracy.

Once a joining waveform is detected by the joining waveform detecting means, the characteristic feature extracting means extracts a characteristic feature indicative of a certain characteristic during the bonding process. The characteristic feature extracted here has a correlation with a post-durability-test physical quantity based on which a quality required for the joint after a durability test can be evaluated, and is predetermined. Characteristic features may include, for example, an inflection point or gradient (change rate) of the joining waveform. The post-durability-test physical quantities may be any properties of the joint that change over time and include, for example, the post-durability-test bonding area, post-durability-test tensile strength, resistance of the joint.

After that, the quality evaluation means compares the characteristic feature extracted by the characteristic feature extracting means with the characteristic feature in the bonding process in which good joint quality is ensured to evaluate the joint quality of the joint based on the replication probability of the bonding process. For example, if a bonding process equivalent to the bonding process in which good joint quality is ensured is being reproduced, the joint quality may be evaluated as good, while, if it is not being reproduced, the joint quality may be evaluated as no good. Since the characteristic feature extracted by the characteristic feature extracting means has a correlation with a post-durability-test physical quantity, the replication probability of the bonding process can be evaluated accurately by evaluating the characteristic feature. As a result, the joint quality of the joint can be inspected accurately.

Moreover, with the joint quality inspection apparatus according to the present invention, the joining waveforms are detected during the bonding process and processing in respective means is performed instantaneously after the bonding, so that joint quality of each one of the products can be inspected in real time. Namely, a 100% joint quality inspection can be achieved. Accordingly, with the joint quality inspection apparatus according to the present invention, the joint quality of all the products can be inspected accurately in real time.

Another aspect of the present invention made to solve the above problem provides a joint quality inspection apparatus for inspecting a quality of a joint formed through ultrasonic joining of a bonding item to a bonding target member by applying ultrasound to a tool while pressing the bonding item with the tool, the apparatus comprising: a joining waveform detecting means for detecting at least one of joining waveforms generated during a bonding process; a characteristic feature extracting means for extracting, from the joining waveform detected by the joining waveform detecting means, a characteristic feature having a correlation with a post-durability-test physical quantity based on which a quality required for the joint after a durability test can be evaluated; a memory means for preliminarily storing therein an equation for calculating the post-durability-test physical quantity; a post-durability-test physical quantity calculating means for calculating the post-durability-test physical quantity of the joint from the characteristic feature extracted by the characteristic feature extracting means using the equation stored in the memory means; and a quality evaluation means for evaluating the joint quality of the joint based on a comparison between the post-durability-test physical quantity calculated by the post-durability-test physical quantity calculating means and a predetermined threshold.

In this joint quality inspection apparatus, at least one of the joining waveforms generated during the bonding process is detected by the joining waveform detecting means. Here, it is preferable to detect joining waveforms associated with a deformation amount of the bonding item and an amplitude of the tool by the joining waveform detecting means. It is even more preferable to also detect a joining waveform associated with a vibration frequency of the tool.

This is because, by thus detecting a plurality of joining waveforms, the joint quality can be evaluated with improved accuracy.

Once a joining waveform is detected by the joining waveform detecting means, the characteristic feature extracting means extracts a predetermined characteristic feature. The characteristic feature extracted here, as mentioned above, also has a correlation with a post-durability-test physical quantity based on which a quality required for the joint after a durability test can be evaluated, and is predetermined.

Next, the post-durability-test physical quantity calculating means calculates the post-durability-test physical quantity of the joint from the characteristic feature extracted by the characteristic feature extracting means using the equation stored in the memory means. Thus the post-durability-test physical quantity of the joint can be calculated (estimated) accurately. The equation may be, for example, a multiple regression equation indicative of a correlative relationship between the characteristic feature in the bonding process in which good joint quality is ensured and the post-durability-test physical quantity.

While the post-durability-test physical quantities of the joint may include the post-durability-test bonding area, post-durability-test tensile strength, resistance of the joint, and the like, the post-durability-test bonding area is particularly suitable. This is because, with the use of post-durability-test bonding area representing the post-durability-test physical quantity of the joint, it can be accurately determined whether or not a current flow area required after the durability test is secured.

For this purpose, in the joint quality inspection apparatus according to the present invention, preferably, the memory means stores therein a multiple regression equation derived from a preliminary multiple regression analysis to obtain a correlative relationship between the characteristic feature in the bonding process in which good joint quality is ensured and the post-durability-test physical quantity, and the post-durability-test physical quantity calculating means calculates a post-durability-test bonding area of the joint from the characteristic feature extracted by the characteristic feature extracting means using this multiple regression equation. The multiple regression equation preset in the memory means should preferably have a multiple correlation coefficient of 0.8 or more in order to ensure calculation accuracy of the post-durability-test physical quantity of the joint.

Once the post-durability-test physical quantity of the joint is calculated, the quality evaluation means evaluates the joint quality of the joint based on a comparison between this calculated post-durability-test physical quantity and a predetermined threshold. A lower reference limit, for example, may be set as the threshold, so that, if the calculated post-durability-test physical quantity (i.e., bonding area, etc) is equal to or more than the threshold (lower reference limit), the joint quality is determined as good, whereas, if the calculated post-durability-test physical quantity (i.e., bonding area, etc) is lower than the threshold (lower reference limit), the joint quality is determined as no good. In this way, with the joint quality inspection apparatus according to the present invention, the joint quality of the joint can be inspected accurately.

With the joint quality inspection apparatus according to the present invention, the joining waveforms are detected during the bonding process and processing in respective means is performed instantaneously after the bonding, so that the joint quality inspection can be carried out to each of the products in real time. Namely, a 100% joint quality inspection can be achieved. Accordingly, with the joint quality inspection apparatus according to the present invention, the joint quality of all the products can be inspected accurately in real time.

Note, when evaluating the joint quality based on the post-durability-test physical quantity, even when the joining waveform detected by the joining waveform detecting means is not reproducing the joining waveform generated in the bonding process in which good joint quality is ensured, depending on the combination of data of characteristic features, in rare occasions, a joint that should actually be determined as no good (NO) may be erroneously determined as good (OK).

Therefore, the joint quality inspection apparatus according to the present invention should preferably further include a replication probability evaluation means for evaluating the replication probability of the bonding process by comparing the characteristic feature extracted by the characteristic feature extracting means and the characteristic feature in a bonding process in which good joint quality is ensured, wherein the quality evaluation means determines the joint quality of the joint as good only when the replication probability evaluation means determines the replication probability of the bonding process as good and the joint quality is determined as good by evaluation based on the post-durability-test physical quantity calculated by the post-durability-test physical quantity calculating means.

Thereby, an erroneous judgment of the joint quality as being good even when the joining waveform detected by the joining waveform detecting means is not reproducing the joining waveform generated in a bonding process in which good joint quality is ensured, i.e., even when the replication probability of the bonding process is lacking, can be eliminated. Therefore, the accuracy of the joint quality inspection is further enhanced.

Another aspect of the present invention made to solve the above problem provides a joint quality inspection method for inspecting a quality of a joint formed through ultrasonic joining of a bonding item to a bonding target member by applying ultrasound to a tool while pressing the bonding item with the tool, the method comprising: a joining waveform detecting step of detecting at least one of joining waveforms generated during a bonding process; a characteristic feature extracting step of extracting, from the joining waveform detected in the joining waveform detecting step, a characteristic feature having a correlation with a post-durability-test physical quantity based on which a quality required for the joint after a durability test can be evaluated; and a quality evaluation step of evaluating the joint quality of the joint based on evaluation of replication probability of a bonding process in which good joint quality is ensured by comparing the characteristic feature extracted in the characteristic feature extracting step with a characteristic feature of that bonding process.

In this joint quality inspection method, at least one of the joining waveforms generated during the bonding process is detected in the joining waveform detecting step. Here, it is preferable to detect joining waveforms associated with a deformation amount of the bonding item and an amplitude of the tool in the joining waveform detecting step, and it is even more preferable to also detect a joining waveform associated with a vibration frequency of the tool. This is because, by thus detecting a plurality of joining waveforms, the replication probability of the bonding process can be evaluated with improved accuracy.

Once a joining waveform is detected in the joining waveform detecting step, a characteristic feature indicative of a certain characteristic during the bonding process is extracted in the characteristic feature extracting step. The characteristic feature extracted here has a correlation with a post-durability-test physical quantity based on which a quality required for the joint after a durability test can be evaluated, and is predetermined.

After that, in the quality evaluation step, the characteristic feature extracted in the characteristic feature extracting step is compared with the characteristic feature in the bonding process in which good joint quality is ensured to evaluate the joint quality of the joint based on the replication probability of the bonding process. For example, if a bonding process equivalent to the bonding process in which good joint quality is ensured is being reproduced, the joint quality may be evaluated as good, while, if it is not being reproduced, the joint quality may be evaluated as no good. Since the characteristic feature extracted in the characteristic feature extracting step has a correlation with a post-durability-test physical quantity, the replication probability of the bonding process can be evaluated accurately by evaluating the characteristic feature. As a result, the joint quality of the joint can be inspected accurately.

Moreover, with the joint quality inspection method according to the present invention, the joining waveforms are detected during the bonding process and processing in respective steps is performed instantaneously after the bonding, so that the joint quality of each one of the products can be inspected in real time. Namely, a 100% joint quality inspection can be achieved. Accordingly, with the joint quality inspection method according to the present invention, the joint quality of all the products can be inspected accurately in real time.

Another embodiment of the present invention made to solve the above problem provides a joint quality inspection method for inspecting a quality of a joint formed through ultrasonic joining of a bonding item to a bonding target member by applying ultrasound to a tool while pressing the bonding item with the tool, the method comprising: a joining waveform detecting step of detecting at least one of joining waveforms generated during a bonding process; a characteristic feature extracting step of extracting, from the joining waveform detected in the joining waveform detecting step, a characteristic feature having a correlation with a post-durability-test physical quantity based on which a quality required for the joint after a durability test can be evaluated; a post-durability-test physical quantity calculating step of calculating the post-durability-test physical quantity of the joint from the characteristic feature extracted in the characteristic feature extracting step using an equation for calculating the post-durability-test physical quantity; and a quality evaluation step of evaluating the joint quality of the joint based on a comparison between the post-durability-test physical quantity calculated in the post-durability-test physical quantity calculating step and a predetermined threshold.

In this joint quality inspection method, at least one of the joining waveforms generated during the bonding process is detected in the joining waveform detecting step. Here, it is preferable to detect joining waveforms associated with a deformation amount of the bonding item and an amplitude of the tool in the joining waveform detecting step. It is even more preferable to also detect a joining waveform associated with a vibration frequency of the tool. This is because, by thus detecting a plurality of joining waveforms, the replication probability of the bonding process can be evaluated with improved accuracy.

Once a joining waveform is detected in the joining waveform detecting step, a predetermined characteristic feature is extracted in the characteristic feature extracting step. The characteristic feature extracted here, as mentioned above, also has a correlation with a post-durability-test physical quantity based on which a quality required for the joint after a durability test can be evaluated, and is predetermined.

Next, in the post-durability-test physical quantity calculating step, the post-durability-test physical quantity of the joint is calculated from the characteristic feature extracted by the characteristic feature extracting means using the equation preliminarily stored in a memory means or the like. Thus the post-durability-test physical quantity of the joint can be calculated (estimated) accurately.

While the post-durability-test physical quantities of the joint may include the post-durability-test bonding area, post-durability-test tensile strength, resistance of the joint, and the like, the post-durability-test bonding area is particularly suitable. This is because, with the use of post-durability-test bonding area representing the post-durability-test physical quantity of the joint, it can be accurately determined whether or not a current flow area required after the durability test is secured.

For this purpose, in the joint quality inspection method according to the present invention, preferably, the post-durability-test physical quantity calculating step includes calculating the post-durability-test bonding area of the joint from the characteristic feature extracted in the characteristic feature extracting step, using a multiple regression equation derived from a preliminary multiple regression analysis to obtain a correlative relationship between the characteristic feature in the bonding process in which good joint quality is ensured and the post-durability-test physical quantity. The multiple regression equation preset should preferably have a multiple correlation coefficient of 0.8 or more in order to ensure calculation accuracy of the post-durability-test physical quantity of the joint.

Once the post-durability-test physical quantity of the joint is calculated, in the quality evaluation step, the joint quality of the joint is evaluated based on a comparison between this calculated post-durability-test physical quantity and a predetermined threshold. A lower reference limit, for example, may be set as the threshold, so that, if the calculated post-durability-test physical quantity (i.e., bonding area, etc) is equal to or more than the threshold (lower reference limit), the joint quality is determined as good, whereas, if the calculated post-durability-test physical quantity (i.e., bonding area, etc) is lower than the threshold (lower reference limit), the joint quality is determined as no good. In this way, with the joint quality inspection method according to the present invention, the joint quality of the joint can be inspected accurately.

With the joint quality inspection method according to the present invention, the joining waveforms are detected during the bonding process and processing in respective steps is performed instantaneously after the bonding, so that the joint quality of each of the products can be inspected in real time. Namely, a 100% joint quality inspection can be achieved. Accordingly, with the joint quality inspection method according to the present invention, the joint quality of all the products can be inspected accurately in real time.

Note that, when evaluating the joint quality based on the post-durability-test physical quantity, even when the joining waveform detected in the joining waveform detecting step is not reproducing the joining waveform generated in a bonding process in which good joint quality is ensured, depending on the combination of data of characteristic features, in rare occasions, a joint that should actually be determined as no good (NG) may be erroneously determined as good (OK).

Therefore, the joint quality inspection method according to the present invention should preferably further include a replication probability evaluation step of evaluating replication probability of the bonding process by comparing the characteristic feature extracted in the characteristic feature extracting step and the characteristic feature in the bonding process in which good joint quality is ensured, wherein in the quality evaluation step includes determining the joint quality of the joint as good only when the replication probability of the bonding process is determined as good in the replication probability evaluation step and the joint quality is determined as good by evaluation based on the post-durability-test physical quantity calculated in the post-durability-test physical quantity calculating step.

Thereby, an erroneous judgment of the joint quality as being good even when the joining waveform detected in the joining waveform detecting step is not reproducing the joining waveform generated in a bonding process in which good joint quality is ensured, i.e., even when the replication probability of the bonding process is lacking, can be eliminated. Therefore, the accuracy of the joint quality inspection is further enhanced.

Effects of the Invention

With the joint quality inspection apparatus and joint quality inspection method according to the present invention, as described above, the joint quality including its reliability of all of the products having bonding items joined to bonding target members can be inspected accurately in real time.

BRIEF DESCRIPTION OF THE DRAWINGS

FIG. 6 is a diagram showing correlation coefficients of standard data of respective characteristic features;

DESCRIPTION OF THE REFERENCE SIGNS

Figure 1:
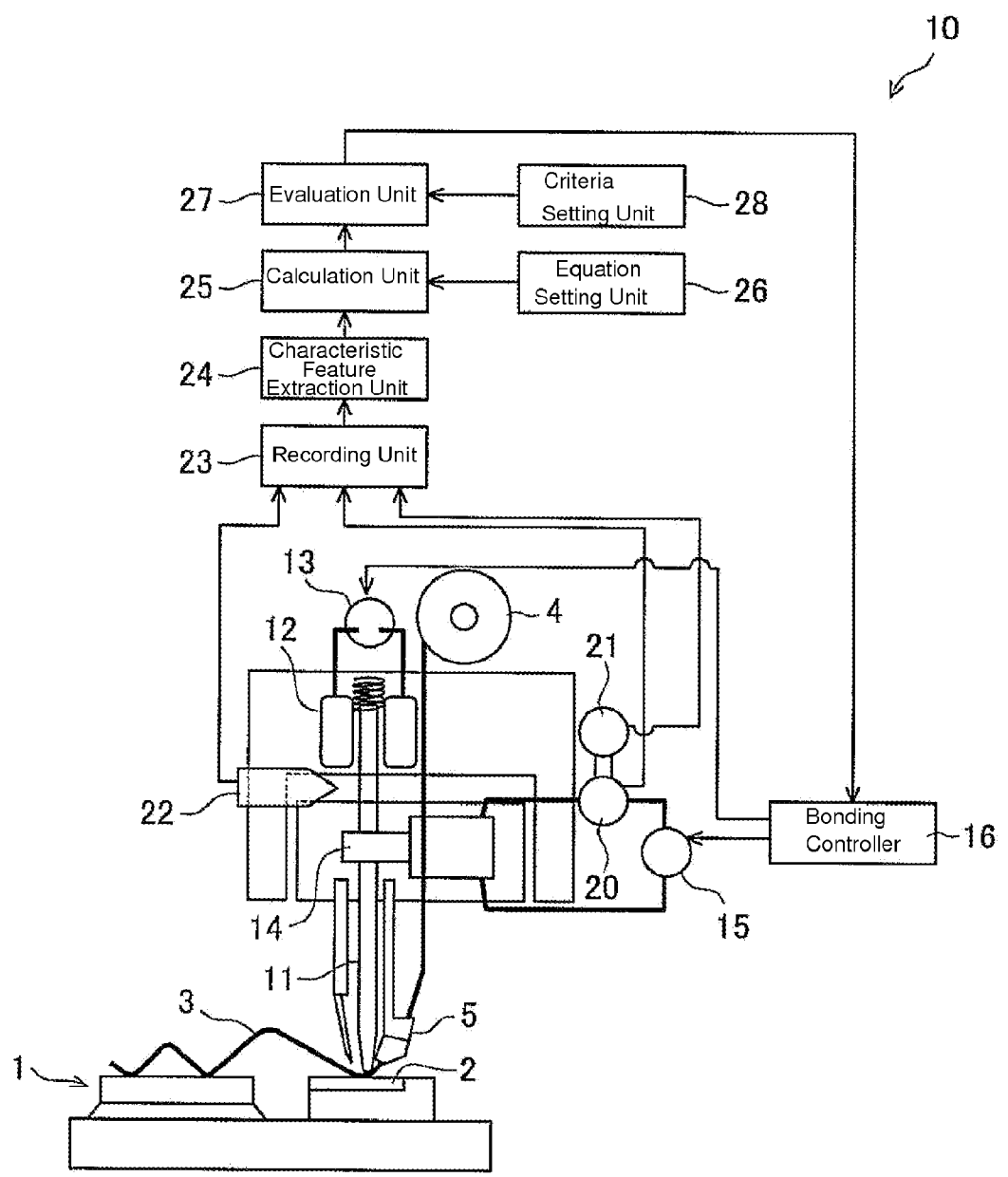
FIG. 1 is a diagram illustrating a schematic configuration of a bonding apparatus according to an embodiment.

1 IGBT device
2 Wiring terminal
3 Wire
4 Bobbin
5 wire feeder/holder
6 Joint
10 Bonding apparatus
11 Tool
12 Electromagnetic coil 13 Drive power source
14 Ultrasonic vibration generator
15 Drive power source
16 Bonding controller
20 Ammeter
21 Frequency meter
22 Encoder
23 Recording unit
24 Characteristic feature extracting unit
25 Calculation unit
26 Equation setting unit
27 Evaluation unit
28 Criteria setting unit

MODE FOR CARRYING OUT THE INVENTION

Figure 2:
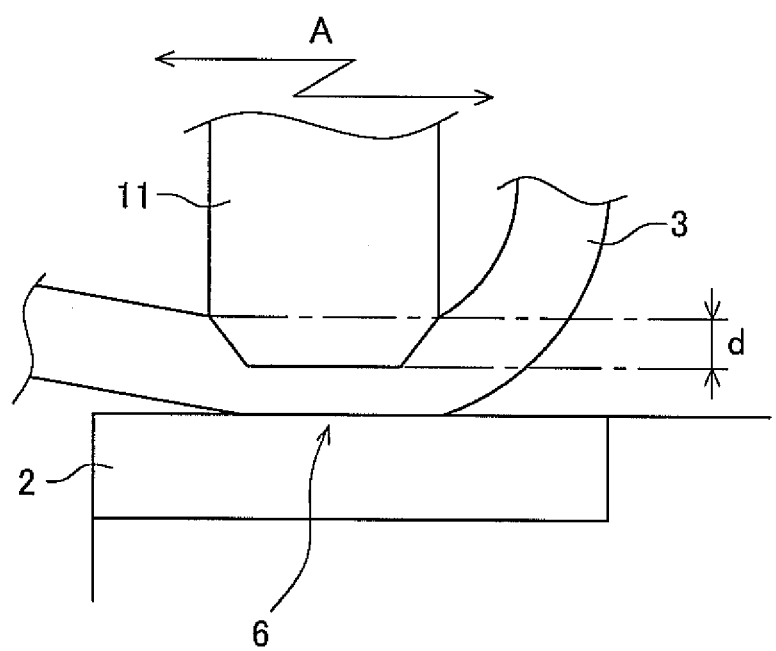
FIG. 2 is an enlarged view of a joint and its vicinity.

Hereinafter, preferred embodiments of the joint quality inspection apparatus and joint quality inspection method according to the present invention will be described in detail with reference to the accompanying drawings. Here, one example in which the present invention is applied to a bonding apparatus for ultrasonically joining a wire (bonding item) to a wiring terminal (bonding target member) of an IGBT device will be illustrated. The bonding apparatus according to the embodiment will now be described with reference to FIGS. 1 and 2. FIG. 1 is a diagram illustrating the schematic configuration of the bonding apparatus according to the embodiment. FIG. 2 is an enlarged view of a joint and its vicinity.

As shown in FIG. 1, a bonding apparatus 10 according to this embodiment includes a tool 11 for the ultrasonic joining of a wire 3 to an IGBT device 1 and a wiring terminal 2. The tool 11 is a bar-like member and formed with grooves (irregularities) in the distal end face (wire pressing surface). An electromagnetic coil 12 is disposed in the proximal end part (opposite to the joint) of the tool 11. A drive power source 13 is connected to this electromagnetic coil 12. Electric power is supplied from the drive power source 13 to the electromagnetic coil 12 in accordance with drive instructions from a bonding controller 16 for the tool 11 to press the wire 3. An ultrasonic vibration generator 14 is disposed near the center of the tool 11. A drive power source 15 is connected to this ultrasonic vibration generator 14. Electric power is supplied from the drive power source 15 to the ultrasonic vibration generator 14 in accordance with drive instructions from the bonding controller 16 for the tool 11 to undergo ultrasonic vibration. As the tool 11 undergoes ultrasonic vibration while pressing down the wire 3 with its tip onto the wiring terminal 2, the wire 3 is ultrasonically joined to the wiring terminal 2. The wire 3 is fed to below the tool 11 from a bobbin 4 via a wire feeder/holder 5.

The bonding apparatus 10 further includes an ammeter 20, a frequency meter 21, and an encoder 22 for detecting operation conditions of the tool 11, and a recording unit 23 for accumulating data detected by these sensors to obtain joining waveforms. The ammeter 20, the frequency meter 21, and the encoder 22 are respectively connected to the recording unit 23, so that data detected respectively by the ammeter 20, the frequency meter 21, and the encoder 22 are sent to and accumulated in the recording unit 23 to obtain respective joining waveforms. In this embodiment, the ammeter 20, the frequency meter 21, the encoder 22, and the recording unit 23 form the "joining waveform detecting means" of the present invention.

The ammeter 20 detects the electric current flowing in the ultrasonic vibration generator 14. The electric current detected by the ammeter 20 here indicates the vibration speed of the tool 11. When the frequency is constant, the vibration speed is proportional to the amplitude A of the tool 11 (see FIG. 2). Namely, by detecting the electric current flowing in the ultrasonic vibration generator 14 with the ammeter 20, a joining waveform associated with the amplitude A of the tool 11 shown in FIG. 2 can be obtained in the recording unit 23.

The frequency meter 21 detects the vibration frequency of the tool 11. By detecting the vibration frequency of the ultrasonic vibration generator 14 with this frequency meter 21, a joining waveform associated with the vibration frequency of the tool 11 can be obtained in the recording unit 23.

The encoder 22 detects displacement of the tool 11 in the vertical direction. The displacement of the tool 11 in the vertical direction detected by the encoder 22 here indicates a deformed amount d of the wire 3 (see FIG. 2). Therefore, by detecting the displacement of the tool 11 in the vertical direction with the encoder 22, a joining waveform associated with the deformed amount d of the wire 3 shown in FIG. 2 can be obtained in the recording unit 23.

Measurement (detection) of respective data by the ammeter 20, the frequency meter 21, and the encoder 22 is performed from the start to the end of bonding with a time interval of 1 msec or less.

In order to inspect (evaluate) the joint quality of the joint 6 between the wiring terminal 2 and the wire 3 based on the joining waveforms obtained in the recording unit 23, the bonding apparatus 10 further includes a characteristic feature extracting unit 24, a calculation unit 25, an equation setting unit 26, an evaluation unit 27, and a criteria setting unit 28.

The characteristic feature extracting unit 24 extracts predetermined characteristic features from respective joining waveforms obtained in the recording unit 23. This characteristic feature extracting unit 24 extracts a plurality of characteristic features from respective joining waveforms. The characteristic features extracted by the characteristic feature extracting unit 24 are inflection points or gradients that appear on respective joining waveforms corresponding to predetermined phenomena that occur during the bonding process (ultrasonic joining process) of bonding the wire 3 to the wiring terminal 2. Here, characteristic features that have a correlation with a physical quantity after a durability test are predetermined. The physical quantity after a durability test is a physical quantity that changes over time, based on which a desirable quality after the durability test can be evaluated. It includes, for example, bonding area after the durability test, tensile strength after the durability test, electrical resistance of the joint, and the like.

Figure 3:
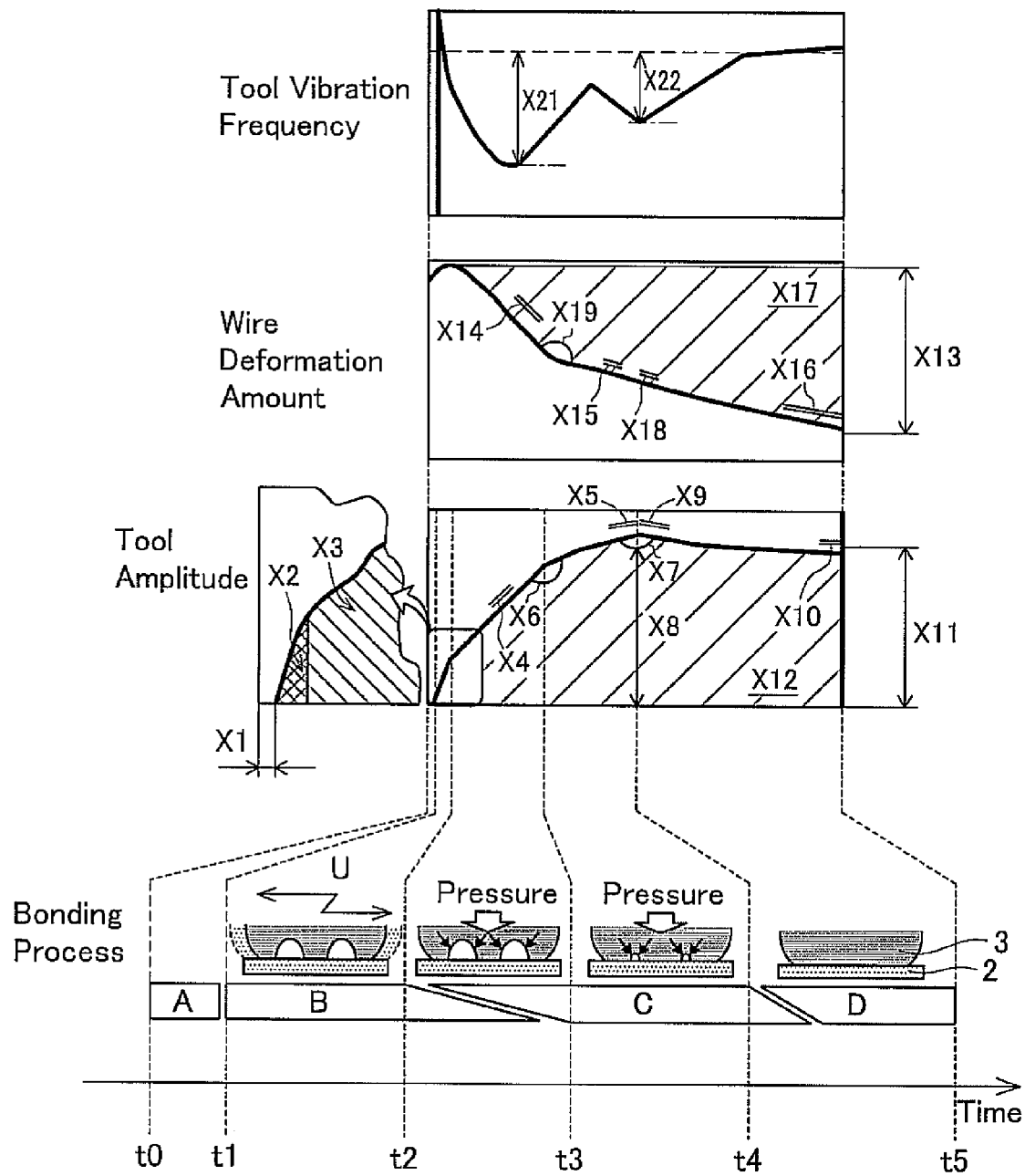
FIG. 3 is a diagram illustrating joining waveforms during a bonding process and characteristic features that appear on the joining waveforms.

Now, the joining waveforms and characteristic features will be described with reference to FIG. 3 and Table 1. FIG. 3 is a diagram illustrating the joining waveforms during a bonding process and characteristic features that appear on the joining waveforms. Table 1 is a list of characteristic features.

The process of bonding the wire 3 and the wiring terminal 2 together is roughly divided into a stationary state, an oxide film removing state, a bonding area increasing state, and a stabilizing state as shown in FIG. 3 and proceeds in this order. More specifically, the bonding starts at time t0, and at time t1, drive force of the tool 11 exceeds the static friction resistance and the wire 3 starts to move toward the wiring terminal 2 (the stationary state to the oxide film removing state). Thereby, after time t1, the oxide film will gradually be removed at the joint 6.

At time t2, the oxide film will have been removed and the wire 3 (part corresponding to the protruded portions of the tool 11) begins to be secured to the wiring terminal 2 (the oxide film removing state). After time t2, the wire is secured in more and more points so that the thickness of the wire 3 begins to change (decrease) (the oxide film removing state).

Next, at time t3, the wire 3 fills up the groove portion of the tool 11, whereby the wire 3 (part corresponding to the recessed portion of the tool 11) begins to be bonded to the wiring terminal 2 (the oxide film removing/bonding area increasing state). After time t3, the bonding area of the joint 6 gradually increases as the wire 3 is deformed (bonding area increasing state).

After time t4, the wire 3 is deformed less and less, the joint 6 is hardened (the stabilizing state), and at time t5 the bonding ends.

In the above-described bonding process, three types of joining waveforms shown in FIG. 3, i.e., waveforms associated with the amplitude of the tool 11, the deformed amount of the wire 3, and the vibration frequency of the tool 11, are obtained from the data detected by the ammeter 20, the encoder 22, and the frequency meter 21. There are a plurality of characteristic features on these joining waveforms corresponding to various steps of the bonding process described above. One example list is shown in Table 1 (FIG. 3). The example here illustrates characteristic features regarding a total of twenty-two items with respect to the three types of joining waveforms. In this embodiment, the characteristic feature extracting unit 24 extracts those that have a correlation with a physical quantity after the durability test from the twenty-two characteristic features shown in Table 1. The characteristic feature extracting unit 24 may either extract suitable features from those shown here, or any other characteristic features other than those shown in Table 1.

unit 25 calculates a bonding area after the durability test as the post-durability-test physical quantity. This enables the evaluation unit 27 to determine whether or not a necessary current flow area will be secured after the durability test, so that the joint quality can be inspected accurately.

In the equation setting unit 26, multiple regression equations representing the correlations between characteristic features in the bonding process in which good joint quality is ensured and post-durability-test physical quantities are set as equations. In this embodiment, the equation setting unit 26 stores multiple regression equations with a multiple correlation coefficient of 0.8 or more. Thereby, the calculation unit 25 can accurately calculate (estimate) a post-durability-test bonding area. This also contributes to improved accuracy of the joint quality inspection.

The evaluation unit 27 evaluates the joint quality of the joint 6 between the wiring terminal 2 and the wire 3 based on evaluation of the characteristic features extracted by the characteristic extracting unit 24 (evaluation of replication probability of the bonding process), and evaluation of the post-durability-test physical quantities calculated by the calculation unit 25. The evaluation by the evaluation unit 27 is performed based on respective criteria (thresholds) set in the criteria setting unit 28. The results of evaluation in the evaluation unit 27 are sent to the bonding controller 16. In this embodiment, the criteria set in the criteria setting unit 28 include upper and lower limits of characteristic features for the evaluation of the characteristic features, and a lower reference limit of the post-durability-test bonding area for the evaluation of the post-durability-test bonding area.

TABLE 1

List of characteristic features

| | Parameter names | Calculation | Physical meanings |
| --- | --- | --- | --- |
| X1 | Tool amplitude starting time | | Tool spring constant/Tool fixed resistance |
| X2 | Electrical energy at initial stage of oxide film removal | Integration | Energy before start of oxide film removal |
| X3 | Electrical energy at final stage of oxide film removal | Integration | Energy required for completion of removal of oxide film at tool protrusion |
| X4 | Electric current gradient at initial stage of area increase | ΔAmpere/ΔTime | Wire hardness/Wire joint strength at tool protrusion |
| X5 | Electric current gradient at final stage of area increase | ΔAmpere/ΔTime | Wire hardness/Wire joint strength at tool recess |
| X6 | Electric current change rate at final stage of oxide film removal | Angle | Wire hardness/Wire joint change rate |
| X7 | Change rate at final stage of area increase | Angle | Wire hardness/Wire joint change rate |
| X8 | Electric current indicative of area stabilization | | Wire joint strength |
| X9 | Electric current gradient at final stage of area stabilization | ΔAmpere/ΔTime | Wire hardness/Wire joint strength |
| X10 | Electric current gradient at final stage of area stabilization | ΔAmpere/ΔTime | Wire hardness/Wire joint strength |
| X11 | Electric current at final stage of area stabilization | | Wire joint strength |
| X12 | Electrical energy for entire bonding | Integration | Wire energy |
| X13 | Sinking amount at final stage of area stabilization | | Wire deformation amount |
| X14 | Gradient during area increase | ΔSinking amount/ΔTime | Wire hardness/Wire joint strength at tool protrusion |
| X15 | Gradient at initial stage of area increase | ΔSinking amount/ΔTime | Wire hardness/Wire joint strength at tool recess |
| X16 | Gradient at final stage of stabilization | ΔSinking amount/ΔTime | Wire hardness/Wire joint strength |
| X17 | Energy required for sinking in entire bonding | Integration | Wire deformation energy |
| X18 | Gradient indicative of area stabilization | ΔSinking amount/ΔTime | Wire hardness/Wire joint strength |
| X19 | Change rate at final stage of oxide film removal | Angle | Wire hardness/Wire joint change rate |
| X20 | Energy difference in bonding (X12-X13) | | Bonding energy |
| X21 | Frequency at initial stage of area increase | | Wire hardness/Wire joint strength |
| X22 | Frequency during area stabilization | | Wire hardness/Wire joint strength |

Referring back to FIG. 1, the calculation unit 25 calculates a post-durability-test physical quantity of the joint 6 between the wiring terminal 2 and the wire 3 from the characteristic features extracted by the characteristic feature extracting unit 24. The calculation unit 25 calculates the post-durability-test physical quantity based on an equation predetermined by the equation setting unit 26. In this embodiment, the calculation While the characteristic features and the post-durability-test physical quantities are both evaluated in this embodiment, the joint quality of the joint 6 can be evaluated based on evaluation of only one of these.

Figure 4:
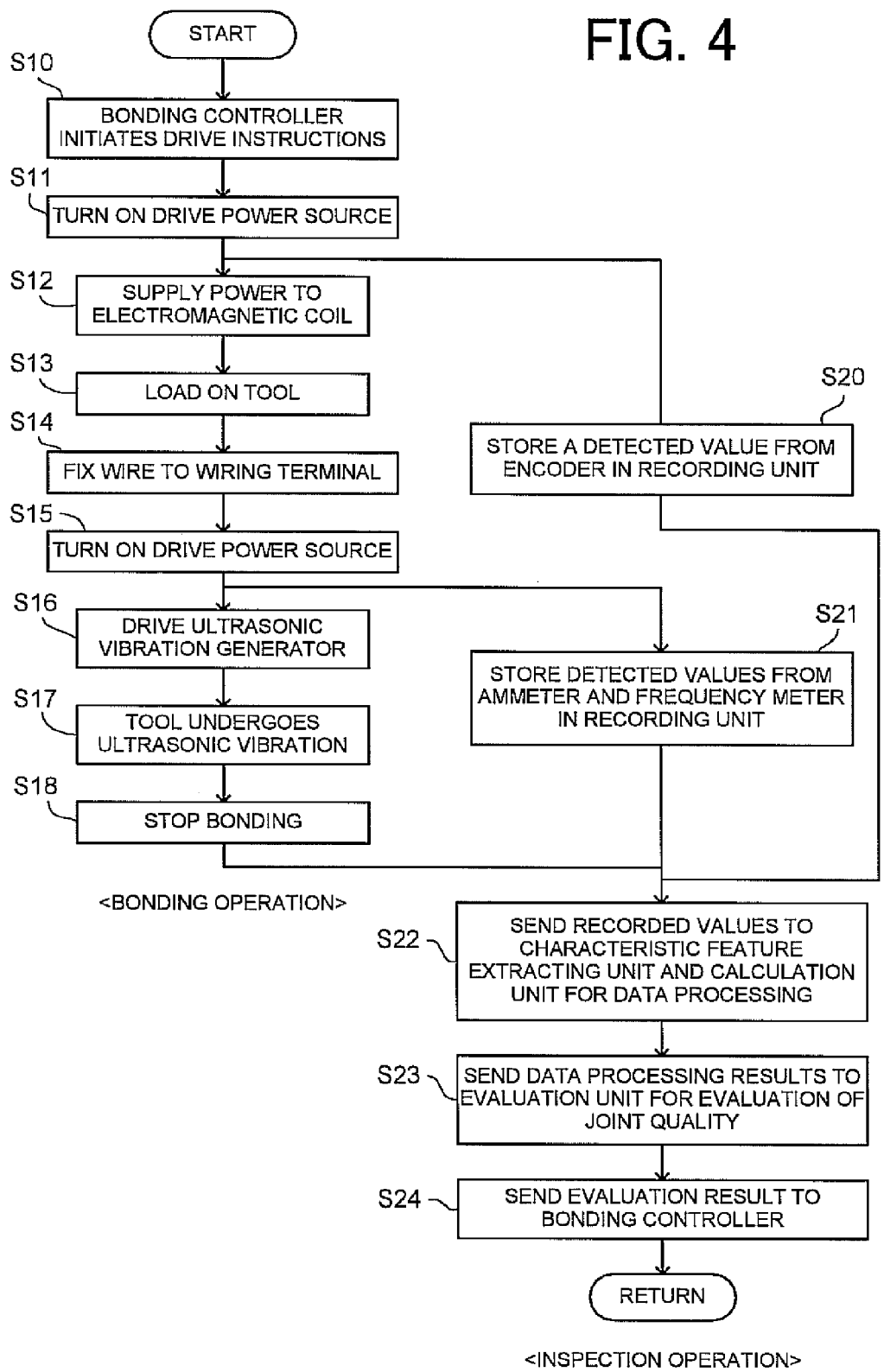
FIG. 4 is a flowchart showing the operation of the bonding apparatus.

Next, the operation of the bonding apparatus 10 configured as described above will be described with reference to FIG. 4. FIG. 4 is a flowchart showing the operation of the bonding apparatus. Since the bonding apparatus 10 performs a joint quality inspection at the same time with the bonding of the wire 3, FIG. 4 shows the bonding operation and inspection operation separately (side by side).

First, the bonding operation in the bonding apparatus 10 will be described. In the bonding apparatus 10, the bonding controller 16 initiates drive instructions to the drive power sources 13 and 15 (step S10). This turns on the drive power source 13 (step S11) and begins power supply to the electromagnetic coil 12 (step S12). An electromagnetic force generated in the electromagnetic coil 12 applies a load (pressing force) on the tool 11 (step S13). As a result, the tool 11 presses the wire 3 and fixes it onto the wiring terminal 2 (step S14).

When the tool 11 sets the wire 3 fixedly on the wiring terminal 2, the drive power source 15 is turned on (step S15), and the ultrasonic vibration generator 14 is driven (step S16). Thereby, the tool 11 undergoes ultrasonic vibration while pressing down the wire 3 with its tip onto the wiring terminal 2 (step S17). The wire 3 is thus ultrasonically joined to the wiring terminal 2. After that, when a preset time (of about several hundreds msec) has passed, the bonding controller 16 ends the drive instructions, whereby the drive power sources 13 and 15 are turned off and the bonding of the wire 3 is ended (step S18).

Next, the inspection operation in the bonding apparatus 10 will be briefly described. In the bonding apparatus 10, when the drive power source 13 is turned on, the encoder 22 detects a displacement in the tool 11 (wire deformed amount), and the detected value is sent to and stored in the recording unit 23 (step S20). When the drive power source 15 is turned on in the bonding apparatus 10, the ammeter 20 detects the electric current flowing in the ultrasonic vibration generator 14 (amplitude of the tool 11), as well as the frequency meter 21 detects the vibration frequency of the ultrasonic vibration generator 14 (vibration frequency of the tool 11). The respective detected values from the ammeter 20 and the frequency meter 21 are sent to and stored in the recording unit 23 (step S21). With these processing in steps S20 and S21, joining waveforms associated with the amplitude of the tool 11, deformed amount of the wire 3, and vibration frequency of the tool 11 are obtained in the recording unit 23.

The recorded values (data) recorded in the recording unit 23 are sent to the characteristic feature extracting unit 24 and the calculation unit 25 where the data is respectively processed (step S22). When the data processing in the characteristic feature extracting unit 24 and calculation unit 25 is complete, respective data processing results are sent to the evaluation unit 27, which evaluates the joint quality based on the data processing results (step S23). After that, the evaluation result is sent to the bonding controller 16 (step S24).

One bonding operation and joint quality inspection are thus over and the operations described above are repeated. In the bonding apparatus 10, as described above, while the wire 3 is being bonded to the wiring terminal 2, its joint quality can be inspected in real time. The bonding apparatus 10 can inspect the joint quality accurately as will be described later.

Also, in the bonding apparatus 10, since joining waveforms are detected during the actual bonding process and data processing in respective units is performed immediately after the bonding, it is possible to inspect the joint quality of each one of the products in real time. In other words, a 100% inspection of the joint quality can be achieved.

Figure 5:
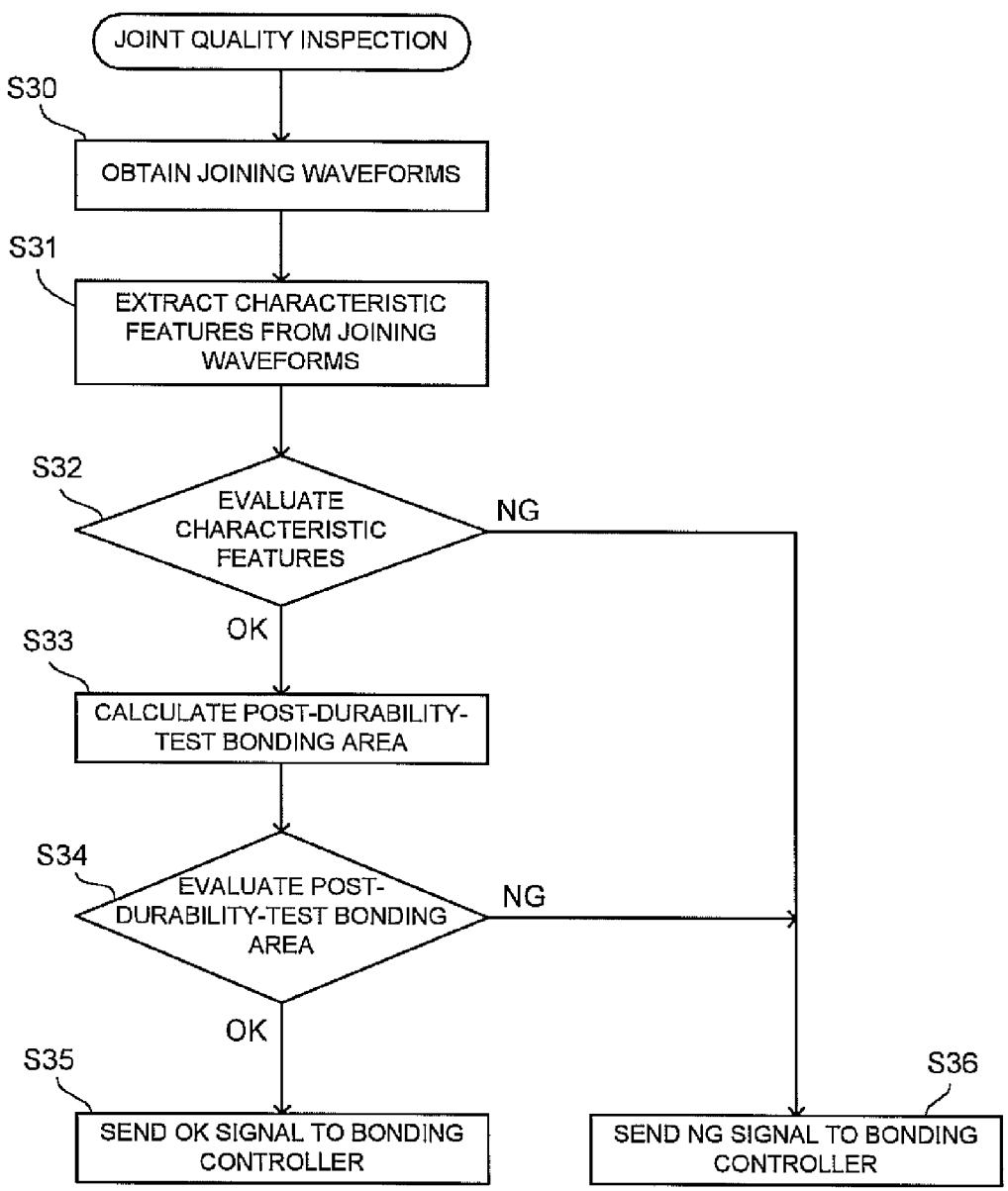
FIG. 5 is a flowchart showing an joint quality inspection operation of the bonding apparatus.

Now, the joint quality inspection operation of the bonding apparatus 10 will be described in more detail with reference to FIG. 5. FIG. 5 is a flowchart showing the joint quality inspection operation of the bonding apparatus.

With the processing in steps S20 and S21 in FIG. 4 described above, three types of joining waveforms, i.e., joining waveforms associated with the wire deformation amount, tool amplitude, and tool vibration frequency are obtained in the recording unit 23 (step S30). Then the characteristic feature extracting unit 24 extracts predetermined characteristic features from the joining waveforms obtained in step S30 (step S31).

When characteristic features are extracted in step S31, the evaluation unit 27 evaluates the extracted characteristic features, i.e., determines the replication probability of a good bonding process (step S32). This evaluation in step S32 is achieved by determining whether or not data of the extracted characteristic features falls within a reference range preset in the criteria setting unit 28. In this embodiment, the reference values for the evaluation consist of an upper limit "Ave+nσ" and a lower limit "Ave−mσ" of the reference range, wherein Ave represents an average value, σ is a standard deviation, and n and m are positive integers, where n=m or n≠m. The reference values for the evaluation set in the criteria setting unit 28 are not restricted to such upper and lower limits described above.

If the evaluation unit 27 determines that the characteristic feature extracted in step S31 falls within the reference range set in the criteria setting unit 28 (approved), the post-durability-test physical quantity (in this embodiment, post-durability-test bonding area) is calculated (step S33).

On the other hand, if the evaluation unit 27 determines that the characteristic feature extracted in step S31 falls out of the reference range set in the criteria setting unit 28 (rejected), it is assumed that the good bonding process is not being reproduced, and therefore an NG signal indicating the characteristic feature being no good, i.e., the joint quality being poor is sent to the bonding controller 16 (step S36). The bonding controller 16 that has received this NG signal carries out a predetermined abnormality processing. This abnormality processing may include, for example, notifying an operator of the occurrence of an abnormality in the apparatus, halting the subsequent bonding operation, removing the defective product, etc.

At step S33, the calculation unit 25 calculates the post-durability-test physical quantity of the joint 6. In this embodiment, the post-durability-test bonding area S is calculated as the post-durability-test physical quantity. The post-durability-test physical quantity is calculated by the equation preset in the equation setting unit. In this embodiment, the following multiple regression equation (1) with a multiple correlation coefficient of 0.8 or more is set as the equation:

$$Y = \beta_1 \times X_1 + \beta_2 \times X_2 + \ldots + \beta_n X_n + \alpha \qquad (1)$$

where Y is the post-durability-test physical quantity, α and βn are regression coefficients, and Xn represents characteristic features (data).

Specific multiple regression equations for calculating the post-durability-test bonding area S as the post-durability-test physical quantity Y will be described in more detail in the description of examples later.

When the post-durability-test bonding area S of the wire 3 is calculated in the calculation unit 25 using the predetermined multiple regression equation (1) given above based on the data of the characteristic features extracted in step S31, the evaluation unit 27 evaluates the calculated post-durability-test bonding area S (step S34). This evaluation in step S34 is performed by a comparison with a reference value preset in the criteria setting unit 28. In this embodiment, a lower limit of the bonding area is set as the reference value for the evaluation. This reference value for the evaluation may be set in accordance with the post-durability-test physical quantity calculated in step S33.

At step S34, if the evaluation unit 27 determines that the post-durability-test bonding area S calculated in step S33 is equal to or more than the lower limit of the bonding area set in the criteria setting unit 28 (approved), it sends an OK signal indicative of the joint quality being good to the bonding controller 16 (step S35). The bonding controller 16 that has received this OK signal carries out the next bonding.

On the other hand, if the evaluation unit 27 determines that the post-durability-test bonding area S calculated in step S33 is less than the lower limit of the bonding area set in the criteria setting unit 28 (rejected), it sends an NG signal indicative of the joint quality being poor to the bonding controller 16 (step S36). The bonding controller 16 that has received this NG signal performs a predetermined abnormality processing.

As described above, the bonding apparatus 10 calculates (estimates) the post-durability-test bonding area from the characteristic features extracted from the joining waveforms using the multiple regression equation (1) with a multiple correlation coefficient of 0.8 or more. Therefore the post-durability-test bonding area is estimated accurately. The joint quality of the joint is evaluated based on this accurately estimated post-durability-test bonding area. Since it is precisely determined whether or not a current flow area required after the durability test is secured, the joint quality can be inspected accurately.

Also, the replication probability of the good bonding process can be determined based on evaluation of the characteristic features extracted from the joining waveforms. Thereby, an erroneous judgment of joint quality as being good even when the good bonding process is not being reproduced, i.e., even when the replication probability of the bonding process is lacking, can be eliminated. Therefore, the accuracy of joint quality inspection can further be enhanced by evaluating the characteristic features in addition to the evaluation of the post-durability-test bonding area.

Next, the steps of inspecting the joint quality using the bonding apparatus 10 will be described with specific figures. The following examples illustrate a case in which a tape-like wire is bonded to a wafer (tape bonding).

Example 1

In Example 1, the joint quality is evaluated based only on the post-durability-test bonding area. That is, the processing in step S32 in FIG. 5 (evaluation of replication probability of the bonding process) is omitted from the inspection operation in the bonding apparatus 10. The joining waveform associated with the tool vibration frequency is not obtained in step S30 in FIG. 5. That is, the post-durability-test bonding area is calculated based on the two types of joining waveforms obtained associated with the wire deformation amount and tool amplitude.

To inspect the joint quality by the bonding apparatus 10, the characteristic features to be extracted in the characteristic feature extracting unit 24 need to be specified beforehand, as well as the equation set in the equation setting unit 26 and reference values set in the criteria setting unit 28 need to be predetermined beforehand. The steps of determining these will now be described.

The characteristic features to be extracted in the characteristic feature extracting unit 24 were selected from those listed in Table 1 described above. More specifically, twenty items X1 to X20 except for the characteristic features regarding the tool vibration frequency were selected as candidates as shown in Table 2. Data was obtained with the number of samples N=629 with respect to these candidate characteristic features. As the data of respective characteristic features are in different units, the data was unified (standardized). The data standardization was achieved by "((each data)−(average value))/(standard deviation)". Based on the unified data (standardized data), the average, standard deviation, skewness, kurtosis, variation coefficient, and variance of respective characteristic features were obtained. Of these, the results of skewness and kurtosis are shown in Table 2. Table 2 is a list of fundamental statistics of standard data of the characteristic features.

Correlation coefficients of respective characteristic features were also obtained. The results are shown in FIG. 6. FIG. 6 is a diagram showing the correlation coefficients of standard data of respective characteristic features. From FIG. 6, it was determined that there existed a collinearity (multicollinearity) between the characteristic features that have a correlation coefficient of 0.9 or more (see shaded cells in FIG. 6). The multicollinearities thus found are shown in Table 2.

Of the twenty characteristic features X1 to X20 mentioned above, thirteen features X2, X3, X5, X6, X8, X9, X12 to X15, X17 to X19 that have a normal skewness, kurtosis, and multicollinearity were selected to be set as the characteristic features extracted by the characteristic feature extracting unit 24. Skewness and kurtosis of an absolute value of 1.5 or more (see shaded cells in Table 2) were determined as abnormal.

TABLE 2

Basic Statistics of Standard Data

| | Parameter Names | Skewness | Kurtosis | Collinearity | Adoptability |
|---|---|---|---|---|---|
| X1 | Rise time | 1.50 | 15.15 | — | X |
| X2 | 13 ms integration | −0.40 | −0.03 | — | O |
| X3 | 40 ms integration | −0.42 | −0.30 | — | O |
| X4 | Gradient at 40 ms | −0.64 | 1.28 | X6 | X |
| X5 | Gradient before 150 ms | 0.85 | 0.10 | — | O |
| X6 | Angle at change point | −0.57 | −0.04 | X4 | O |
| X7 | Angle at 150 ms | −1.11 | 1.82 | — | X |
| X8 | Current at 150 ms | −0.14 | −1.01 | X12, X20 | O |
| X9 | Gradient after 150 ms | −0.43 | 0.01 | — | O |
| X10 | Gradient at 300 ms | 0.49 | 1.92 | — | X |
| X11 | Current at 300 ms | −0.08 | −0.90 | X12 | X |
| X12 | Integration | −0.23 | −1.00 | X11, X20 | O |
| X13 | Sinking amount | −0.15 | −0.30 | — | O |
| X14 | Gradient at 60 ms | −0.09 | −0.22 | — | O |
| X15 | Gradient before 150 ms | 0.51 | 0.06 | — | O |
| X16 | Gradient at 300 ms | −1.15 | 2.57 | — | X |
| X17 | Integration | −0.52 | −0.79 | — | O |
| X18 | Gradient after 150 ms | 0.15 | −0.35 | — | O |
| X19 | Angle at change point | −0.28 | −0.70 | — | O |
| X20 | Difference in integration | −0.33 | −0.93 | X8, X12 | X |

▓ ∥ 1.5 or more

After selecting characteristic features to be extracted by the characteristic feature extracting unit 24 as described above, multiple regression equations to be set in the equation setting unit 26 are determined by multiple regression analysis from these characteristic features. Here, the characteristic features to be extracted by the characteristic feature extracting unit 24 as well as to be used in the multiple regression equation are determined so that the multiple correlation coefficient is 0.8 or more. The characteristic features are determined through calculation until a target multiple correlation coefficient is achieved. In Example 1, X8, X9, X3, X19, and X5 were determined to be the characteristic features to be extracted by the characteristic feature extracting unit 24 as well as to be used in the multiple regression equation.

The equation for calculating the post-durability-test bonding area S from the results of multiple regression analysis here was as follows:

$$S = 0.0587X8 - 0.0287X9 + 0.0112X3 + 0.0065X19 - 0.0086X5 + 0.28215 \quad (2)$$

Figure 7:
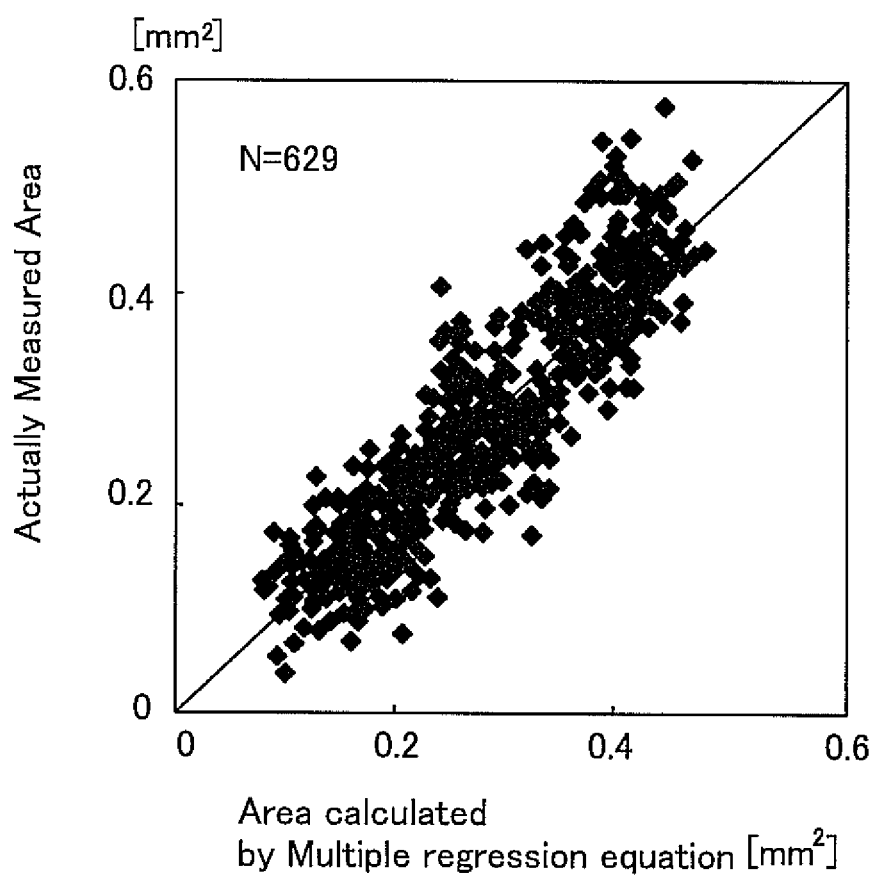
FIG. 7 is a diagram showing a relationship between a post-durability-test bonding area and actually measured area.

The multiple correlation coefficient was 0.89. This equation (2) was then set in the equation setting unit 26. The relationship between the post-durability-test bonding area calculated from the equation (2) and actually measured area is shown in FIG. 7. It can be seen from FIG. 7 that the post-durability-test bonding area can be accurately calculated from the equation (2).

The joint quality inspection was then carried out using the characteristic features set through the procedure described above and the equation (2) to 1,188 samples (N=1188), with a result that the rate of an inspection error wherein poor quality is judged as good was 2.5%.

Example 2

In Example 2, the joining waveform associated with the tool vibration frequency is not obtained either, and the joint quality is evaluated based only on the post-durability-test bonding area. In Example 2, in order to reduce the error inspection rate, significant quadratic terms and interaction terms were added as characteristic features used in the multiple regression equation in addition to X8, X9, X3, X19, and X5. The added items are X2, X2*X8, X8*X9, and X19*X19. Therefore, X2 was added to the characteristic features to be extracted by the characteristic feature extracting unit 24.

The equation for calculating the post-durability-test bonding area S from the results of multiple regression analysis here was as follows:

$$\begin{aligned} S = \quad & (3) \\ 0.0487X8 + (X2 - 0.0007)((X8 + 0.0174) \times (-0.015)) - 0.0197X9 + \\ 0.0276X3 + (X8 + 0.0174)((X9 - 0.0114) \times (-0.0126)) + \\ (X19 - 0.0019)((X19 - 0.0019) \times (-0.0068)) - \\ 0.011X5 - 0.0087X2 + 0.003X19 \end{aligned}$$

Figure 8:
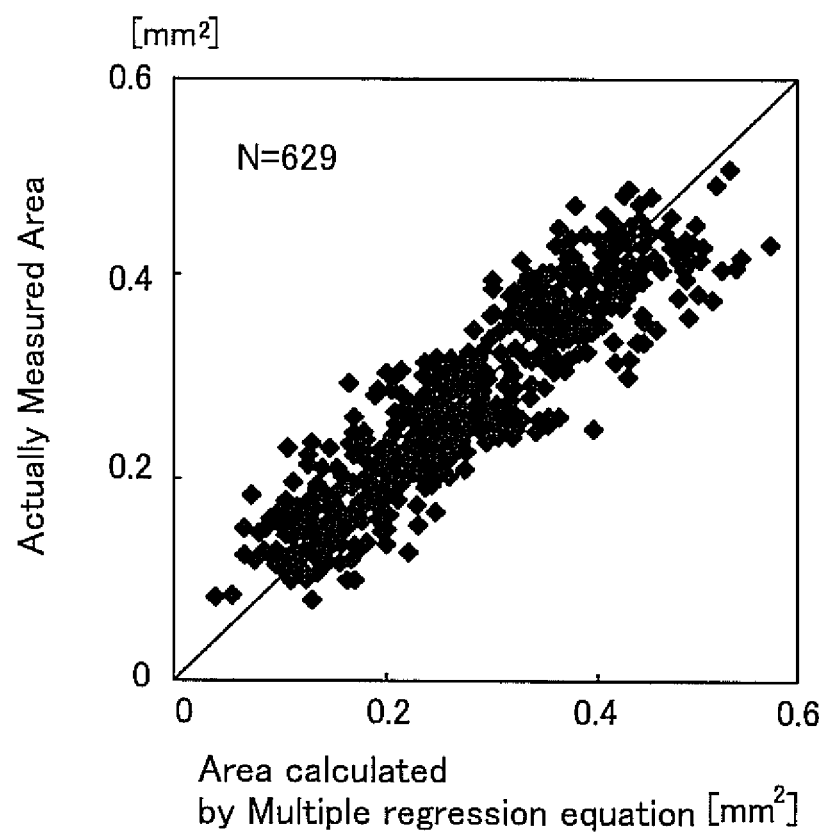
FIG. 8 is a diagram showing a relationship between a post-durability-test bonding area and actually measured area.

The multiple correlation coefficient was 0.92. This equation (3) was then set in the equation setting unit 26. The relationship between the post-durability-test bonding area calculated from the equation (3) and actually measured area is shown in FIG. 8. It can be seen from FIG. 8 that the post-durability-test bonding area can be accurately calculated from the equation (3).

The joint quality inspection was then carried out using the characteristic features set through the procedure described above and the equation (3) to 1,188 samples (N=1188), with a result that the rate of an inspection error wherein poor quality is judged as good was 0.3%.

Instead of adding significant quadratic terms and interaction terms, the joining waveform associated with the tool vibration frequency may be obtained and characteristic features extractable from this waveform (X21, X22) may be added to the characteristic features used in the multiple regression equation. Thereby, the multiple correlation coefficient could be made to 0.90. As a result, the post-durability-test bonding area can be calculated even more accurately than Example 1.

Example 3

In Example 3, to further reduce the error inspection rate, in addition to the evaluation of joint quality based on the post-durability-test bonding area, the joint quality is evaluated based also on the evaluation of characteristic features, i.e., determination of whether or not a good bonding process is being reproduced (replication probability). That is, in the inspection operation of the bonding apparatus 10, the processing in step S32 in FIG. 5 is not omitted but carried out. The characteristic features may be evaluated before the evaluation of the post-durability-test bonding area as shown in FIG. 5, or after the evaluation of the post-durability-test bonding area. In Example 3, the joining waveform associated with the tool vibration frequency is not obtained, either.

The characteristic features based on which it is determined whether or not the good bonding process is being reproduced are X2, X3, X5, X8, X9, and X19. These characteristic features are evaluated such that they are determined as replicates (good) if extracted characteristic feature data falls within the range between upper and lower limits preset in the criteria setting unit 28, and not replicates (poor) if the data is out of the range. The upper limit set in the criteria setting unit 28 is 6.5, while the lower limit is −6.5 except for X2, whose lower limit is −2.7.

Then, only when the characteristic features mentioned above are determined as good, the joint quality is evaluated based on the post-durability-test bonding area in a manner as described in Example 2. Thereby, the error inspection rate was made to 0%.

The excessive inspection rate, which is the percent of good-quality welds determined as defective, was almost zero (0.5 ppm or lower) and would not pose any problem in practical applications.

With the joint quality inspection method by the bonding apparatus 10 according to this embodiment as described above in detail, the ammeter 20, the frequency meter 21, the encoder 22, and the recording unit 23 detect joining waveforms generated during the bonding process. The characteristic feature extracting unit 24 extracts predetermined characteristic features that have a correlation with a post-durability-test bonding area from the detected joining waveforms. The calculation unit 25 then calculates the post-durability-test bonding area of the joint 6 from the extracted characteristic features using the multiple regression equation preset in the equation setting unit 26. After that, the evaluation unit 27 evaluates the joint quality of the joint 6 based on a comparison between the calculated post-durability-test bonding area and a lower limit of the area set in the criteria setting unit 28.

Since the multiple regression equation for calculating the post-durability-test bonding area has a multiple correlation coefficient of 0.8 or more, the post-durability-test bonding area of the joint 6 can be accurately calculated. Therefore, the joint quality of the joint 6 can be accurately evaluated.

Moreover, in the bonding apparatus 10, the joining waveforms are detected during the actual bonding process and data processing in respective units is performed instantaneously after the bonding, so that the joint quality inspection can be carried out to each of the products in real time. Namely, a 100% joint quality inspection can be achieved. Accordingly, with the joint quality inspection apparatus according to the present invention, the joint quality including its reliability of all the products can be inspected accurately in real time.

The above embodiments are mere examples and do not give any limitations to the present invention. The present invention may be embodied in other specific forms without departing from the essential characteristics thereof. For instance, the aforementioned embodiments exemplify the invention applied to the bonding of a wire in IGBT, whereas the present invention is not limited thereto and can be applied to a joint subjected to ultrasonic joining.

The invention claimed is:

1. A joint quality inspection apparatus for inspecting a quality of a joint formed through ultrasonic joining of a bonding item to a bonding target member by applying ultrasound to a tool while pressing the bonding item with the tool, the apparatus comprising:
    a joining waveform detecting means for detecting at least one of joining waveforms generated during a bonding process;
    a characteristic feature extracting means for extracting, from the joining waveform detected by the joining waveform detecting means, a characteristic feature having a correlation with a post-durability-test physical quantity based on which a quality required for the joint after a durability test can be evaluated;
    a memory means for preliminarily storing therein an equation for calculating the post-durability-test physical quantity;
    a post-durability-test physical quantity calculating means for calculating the post-durability-test physical quantity of the joint from the characteristic feature extracted by the characteristic feature extracting means using the equation stored in the memory means;
    a quality evaluation means for evaluating the joint quality of the joint based on a comparison between the post-durability-test physical quantity calculated by the post-durability-test physical quantity calculating means and a predetermined threshold; and
    a replication probability evaluation means for evaluating a replication probability of the bonding process by comparing the characteristic feature extracted by the characteristic feature extracting means and a characteristic feature in the bonding process in which good joint quality is ensured,
    wherein the quality evaluation means determines the joint quality of the joint as good only when the replication probability evaluation means determines the replication probability of the bonding process as good and the joint quality is determined as good by evaluation based on the post-durability-test physical quantity calculated by the post-durability-test physical quantity calculating means.

2. A joint quality inspection apparatus for inspecting a quality of a joint formed through ultrasonic joining of a bonding item to a bonding target member by applying ultrasound to a tool while pressing the bonding item with the tool, the apparatus comprising:
    a joining waveform detecting means for detecting at least one of joining waveforms generated during a bonding process;
    a characteristic feature extracting means for extracting, from the joining waveform detected by the joining waveform detecting means, a characteristic feature having a correlation with a post-durability-test physical quantity based on which a quality required for the joint after a durability test can be evaluated;
    a memory means for preliminarily storing therein an equation for calculating the post-durability-test physical quantity;
    a post-durability-test physical quantity calculating means for calculating the post-durability-test physical quantity of the joint from the characteristic feature extracted by the characteristic feature extracting means using the equation stored in the memory means; and
    a quality evaluation means for evaluating the joint quality of the joint based on a comparison between the post-durability-test physical quantity calculated by the post-durability-test physical quantity calculating means and a predetermined threshold,
    wherein the memory means stores therein a multiple regression equation derived from a preliminary multiple regression analysis to obtain a correlative relationship between the characteristic feature in the bonding process in which good joint quality is ensured and the post-durability-test physical quantity, and
    the post-durability-test physical quantity calculating means calculates a post-durability-test bonding area of the joint from the characteristic feature extracted by the characteristic feature extracting means using the multiple regression equation.

3. The joint quality inspection apparatus according to claim 1, wherein the joining waveform detecting means detects joining waveforms associated with a deformation amount of the bonding item and an amplitude of the tool.

4. The joint quality inspection apparatus according to claim 3, wherein the joining waveform detecting means further detects a joining waveform associated with a vibration frequency of the tool.

5. A joint quality inspection method for inspecting a quality of a joint formed through ultrasonic joining of a bonding item to a bonding target member by applying ultrasound to a tool while pressing the bonding item with the tool, the method comprising:
    a joining waveform detecting step of detecting at least one of joining waveforms generated during a bonding process;
    a characteristic feature extracting step of extracting, from the joining waveform detected in the joining waveform detecting step, a characteristic feature having a correlation with a post-durability-test physical quantity based on which a quality required for the joint after a durability test can be evaluated;
    a post-durability-test physical quantity calculating step of calculating the post-durability-test physical quantity of the joint from the characteristic feature extracted in the characteristic feature extracting step using an equation for calculating the post-durability-test physical quantity;
    a quality evaluation step of evaluating the joint quality of the joint based on a comparison between the post-durability-test physical quantity calculated in the post-durability-test physical quantity calculating step and a predetermined threshold; and
    a replication probability evaluation step of evaluating a replication probability of the bonding process by comparing the characteristic feature extracted in the characteristic feature extracting step and a characteristic feature in the bonding process in which good joint quality is ensured,
    wherein in the quality evaluation step includes determining the joint quality of the joint as good only when the replication probability of the bonding process is determined as good in the replication probability evaluation step and the joint quality is determined as good by evaluation based on the post-durability-test physical quantity calculated in the post-durability-test physical quantity calculating step.

6. A joint quality inspection method for inspecting a quality of a joint formed through ultrasonic joining of a bonding item to a bonding target member by applying ultrasound to a tool while pressing the bonding item with the tool, the method comprising:

a joining waveform detecting step of detecting at least one of joining waveforms generated during a bonding process;

a characteristic feature extracting step of extracting, from the joining waveform detected in the joining waveform detecting step, a characteristic feature having a correlation with a post-durability-test physical quantity based on which a quality required for the joint after a durability test can be evaluated;

a post-durability-test physical quantity calculating step of calculating the post-durability-test physical quantity of the joint from the characteristic feature extracted in the characteristic feature extracting step using an equation for calculating the post-durability-test physical quantity; and a quality evaluation step of evaluating the joint quality of the joint based on a comparison between the post-durability-test physical quantity calculated in the post-durability-test physical quantity calculating step and a predetermined threshold, wherein the post-durability-test physical quantity calculating step includes calculating a post-durability-test bonding area of the joint from the characteristic feature extracted in the characteristic feature extracting step, using a multiple regression equation derived from a preliminary multiple regression analysis to obtain a correlative relationship between the characteristic feature in the bonding process in which good joint quality is ensured and the post-durability-test physical quantity.

7. The joint quality inspection method according to claim 5, wherein the joining waveform detecting step includes detecting joining waveforms associated with a deformation amount of the bonding item and an amplitude of the tool.

8. The joint quality inspection method according to claim 7, wherein the joining waveform detecting step further includes detecting a joining waveform associated with a vibration frequency of the tool.

* * * * *